US00PP37844P3

(12) United States Plant Patent
Mansell et al.

(10) Patent No.: US PP37,844 P3
(45) Date of Patent: Nov. 10, 2026

(54) ***NEPENTHES* PLANT NAMED 'NP8016'**

(50) Latin Name: ***Nepenthes* hybrid.**
Varietal Denomination: NP8016

(71) Applicants: Andrea Mansell, Cordalba (AU); Geoffrey Mansell, Cordalba (AU)

(72) Inventors: Andrea Mansell, Cordalba (AU); Geoffrey Mansell, Cordalba (AU)

( * ) Notice: Subject to any disclaimer, the term of this patent is extended or adjusted under 35 U.S.C. 154(b) by 42 days.

(21) Appl. No.: 19/401,681

(22) Filed: Nov. 26, 2025

(65) Prior Publication Data

US 2026/0157253 P1 Jun. 4, 2026

(30) Foreign Application Priority Data

Nov. 29, 2024 (QZ) ..... PBR 2024/2864

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

(56) References Cited

U.S. PATENT DOCUMENTS

PP31,953 P2 * 7/2020 Cantley ..... A01H 6/00
Plt./373

* cited by examiner

*Primary Examiner* — Karen M Redden
(74) *Attorney, Agent, or Firm* — James R. Holm; Plant Novelty Rights, LLC

(57) ABSTRACT

A new and distinct *Nepenthes* plant named 'NP8016' particularly distinguished by a compact, broad spreading-upright plant habit, with basal branching and no lateral branches; epiascidiate shaped leaves comprising a distinctly defined oblong to broadly oblong lower leaf zone and an elongated cylindrical upper pitcher zone; cylindrical pitchers averaging approximately 19.4 cm in length and 3.0 cm in diameter; two fringed axial ridges positioned along the back of the pitcher; unique pitcher coloration pattern consisting of a greyed-green outer surface, fine greyed-purple spotting near the opening, and a greyed-orange lid with a yellow-green center and fine brown dots; and a single short, hooked soft thorn located on the underside of the pitcher lid.

3 Drawing Sheets

Figure 1:
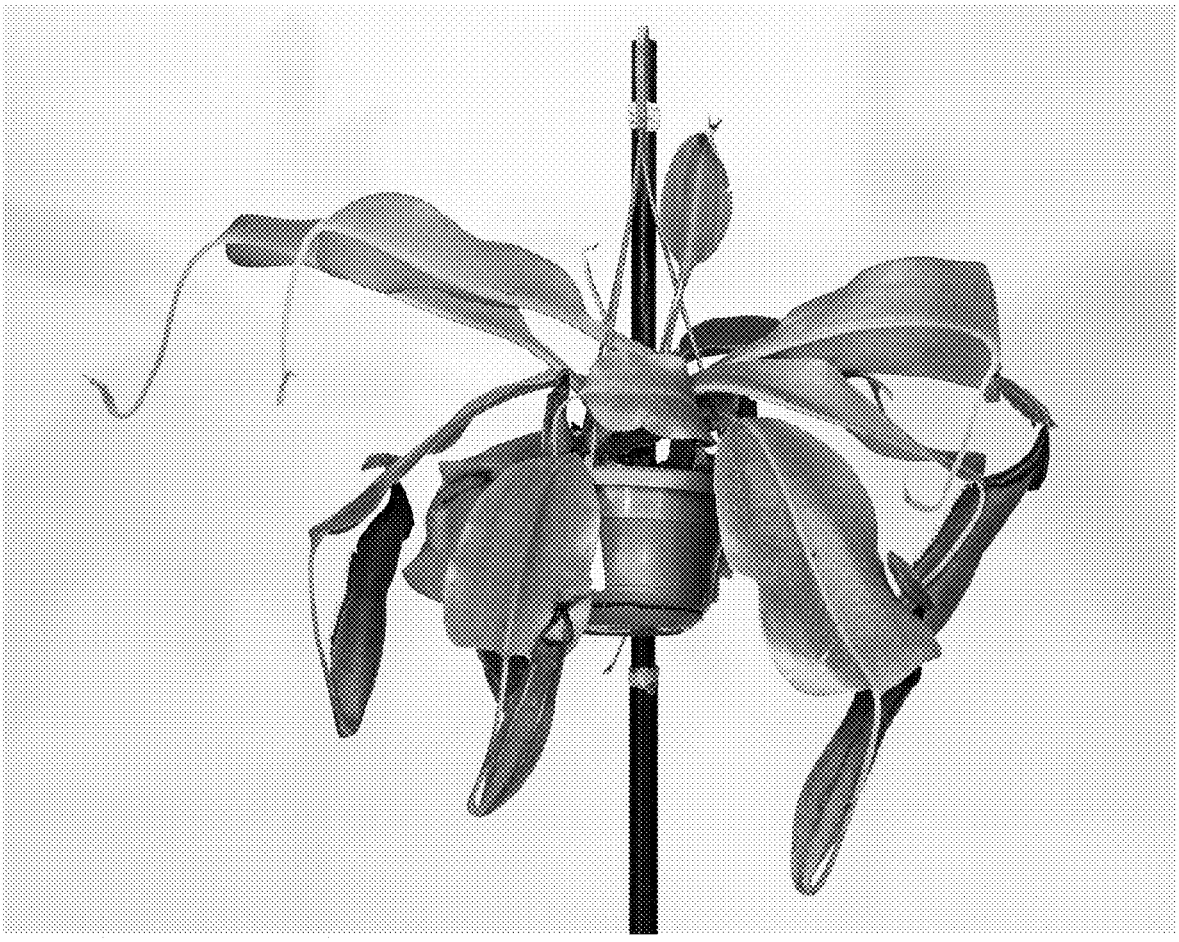

Genus and species: *Nepenthes* hybrid.
Variety denomination: 'NP8016'.

STATEMENT REGARDING PRIOR DISCLOSURES BY THE INVENTOR

This application claims priority to CPVO application no. 2024/2864 filed on Nov. 29, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the effective filing date.

BACKGROUND OF THE NEW PLANT

The present invention comprises a new and distinct variety of *Nepenthes* plant, botanically known as *Nepenthes* hybrid, and hereinafter referred to by the cultivar name 'NP8016'. The new *Nepenthes* variety 'NP8016' is an F1 hybrid seedling selection that resulted from a controlled cross-pollination event conducted by the inventor in September 2021 at a nursery located in Cordalba, Queensland Australia. The controlled cross-pollination was between an unnamed and unpatented *Nepenthes truncata* plant as the female or seed parent, and an unnamed and unpatented *Nepenthes lingulata* plant as the male or pollen parent. Those skilled in the art recognize that *Nepenthes* seed can be difficult to germinate. Therefore, the seed that resulted from the stated cross were shipped by the inventor to a tissue culture laboratory in Evergem, Belgium for in vitro seed germination to increase the germination rate. The resulting seedlings were then shipped back to Cordalba, Queensland Australia for further evaluation by the inventor. In September 2023, a seedling that exhibited potential commercial value was selected from amongst the progeny of the stated cross. This seedling was isolated and allowed to grow to mature size in order to assess the stability of the unique characteristics for which it was selected. Upon confirmation, this new and distinctive *Nepenthes* cultivar was given the name 'NP8016'.

The new *Nepenthes* cultivar 'NP8016' was first reproduced asexually by meristematic tissue culture in November 2023 at a commercial laboratory in Evergem, Belgium. Asexual propagation by meristematic tissue culture of the new variety has shown that the unique features of the new variety are stable and reproduced true-to-type to date through 8 successive generations.

SUMMARY OF THE INVENTION

The new *Nepenthes* cultivar 'NP8016' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Nepenthes* cultivar. The combination of these characteristics distinguishes 'NP8016' as a new and distinct variety of *Nepenthes*.

1. *Nepenthes* 'NP8016' exhibits a compact, broad spreading-upright plant habit, with basal branching and no lateral branches.
2. *Nepenthes* 'NP8016' exhibits epiascidiate shaped leaves comprising a distinctly defined oblong to broadly oblong lower leaf zone and an elongated cylindrical upper pitcher zone.
3. *Nepenthes* 'NP8016' exhibits cylindrical pitchers averaging approximately 19.4 cm in length and 3.0 cm in diameter.
4. *Nepenthes* 'NP8016' exhibits two fringed axial ridges positioned along the back of the pitcher.
5. *Nepenthes* 'NP8016' exhibits a unique pitcher coloration pattern consisting of a greyed-green outer surface, fine greyed-purple spotting near the opening, and a greyed-orange lid with a yellow-green center and fine brown dots.
6. *Nepenthes* 'NP8016' exhibits a single short, hooked soft thorn located on the underside of the pitcher lid.
7. *Nepenthes* 'NP8016' exhibits a pitcher exterior exhibiting moderate pubescence composed of very short adpressed hairs and sparse longer hairs.
8. *Nepenthes* 'NP8016' exhibits a densely pubescent pedicel bearing short, soft grey-white hairs.

DESCRIPTION OF THE PHOTOGRAPHS

This new *Nepenthes* cultivar is illustrated by the accompanying-colored photographs which show the overall appearance and distinct characteristics of the plant. The colors shown are as true as can be reasonably obtained by conventional photographic procedures. The photographs are of 18-month-old plants grown in 14-centimeter circular containers in a conventional glass greenhouse in Evergem, Belgium. Colors in the photographs may differ slightly from the color values cited in the botanical description which accurately describes the colors of the new variety.

FIG. 1. shows the overall plant form and foliage of 'NP8016'.

Figure 2:
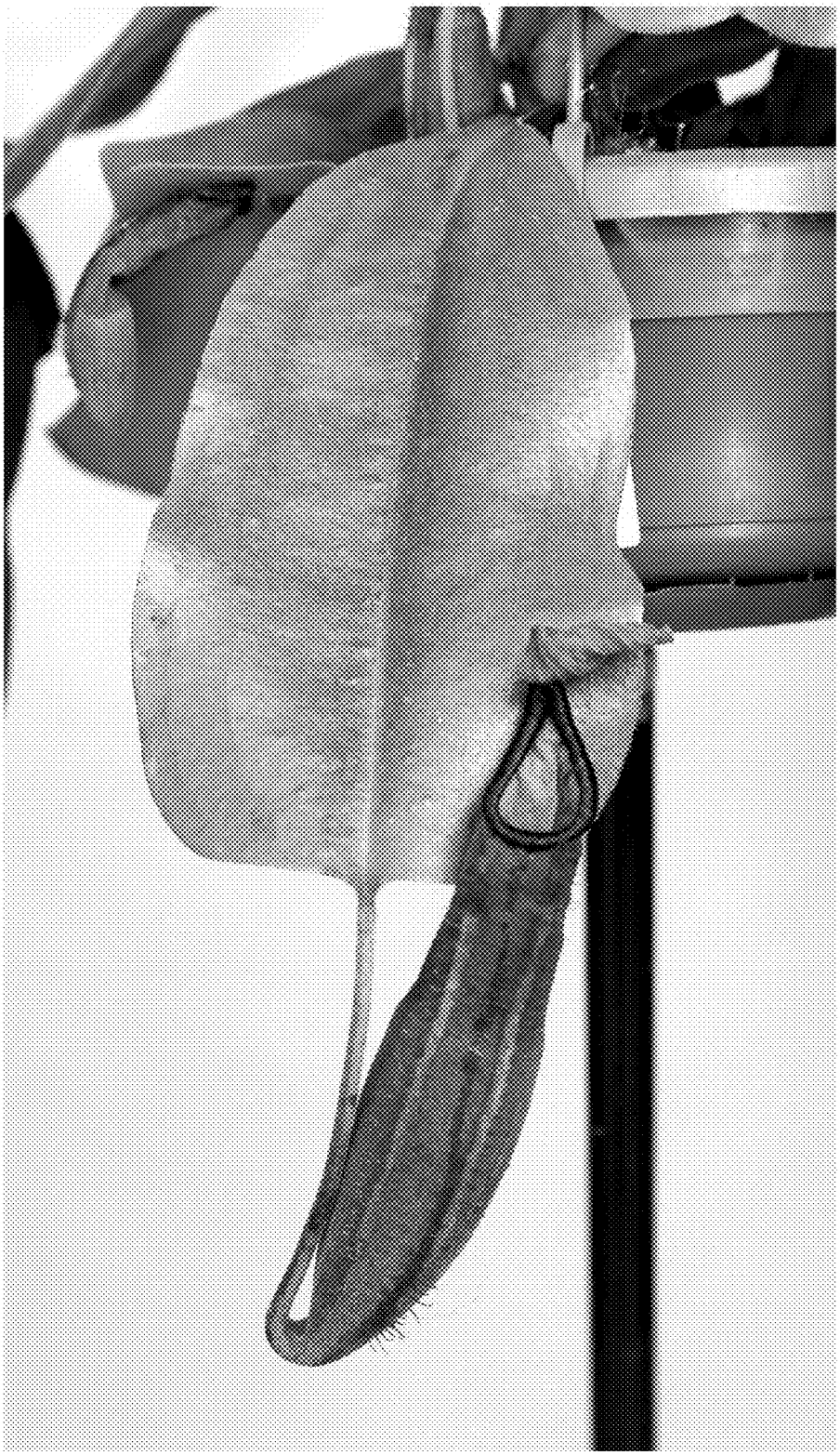

FIG. 2. shows a close-up of the lower leaf zone, or lamina, and the upper leaf zone, or pitcher, of 'NP8016'.

Figure 3:
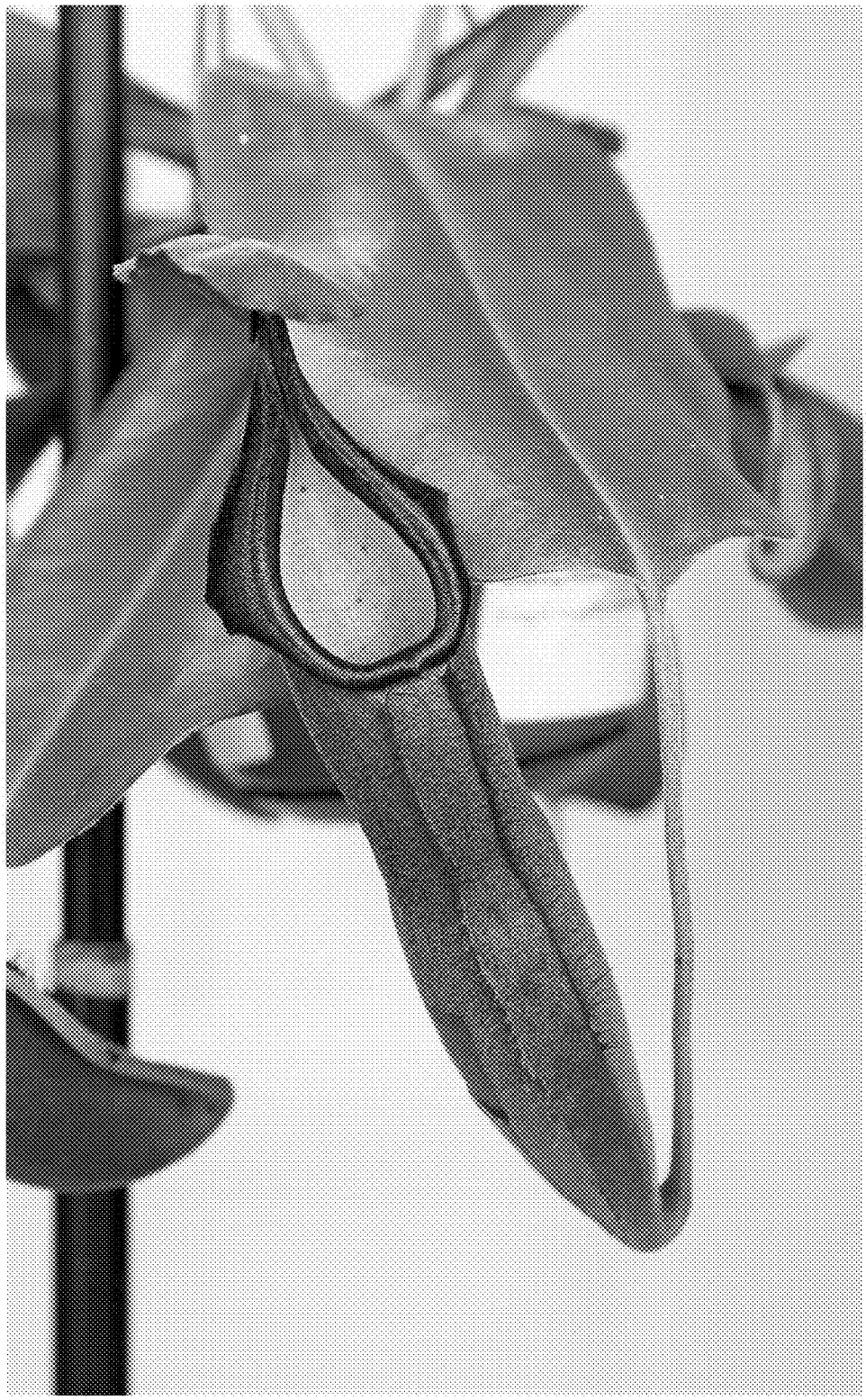

FIG. 3. shows a close-up of a typical pitcher observed on plants of 'NP8016'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Evergem, Belgium. Plants were grown under normal light levels with no supplemental lighting. Average daily temperatures ranged from 21° C. to 23° C. and average nightly temperatures ranged from 19° C. to 21° C. Plants were maintained with a regular fertigation program and regularly watered with overhead irrigation. Detailed descriptions were taken in November 2025 from 18-month-old plants grown in 14-centimeter circular containers. Measurements and numerical values represent averages of typical plant types.

DETAILED BOTANICAL DESCRIPTION

Classification:

*Family*.—Nepenthaceae.

*Botanical: Nepenthes* hybrid.

*Denomination*.—'NP8016'.

Plant description:

*Growth habit*.—Compact, broad and spreading.

*Average height from soil level to top of foliar plane*.—26.8 cm.

*Average height from the base of the pitcher to the top of the foliar plane*.—50.5 cm.

*Plant diameter or area of spread*.—53.3 cm.

*Growth rate and vigor*.—Moderate.

*Propagation type*.—Meristematic tissue culture.

Root description:

*General*.—Fibrous, sparsely branched, and lacking root hairs.

*Distribution in soil profile*.—Moderately deep.

*Density*.—Sparse.

*Diameter*.—Average 0.15 cm.

*Texture*.—Smooth and glabrous.

*Color*.—165C (greyed-orange).

Stems:

*Branching habit*.—Basal branching, no lateral branches present.

*Number of main stems per plant*.—2.

*Appearance and shape*.—Rounded; stems formed by decurrent leaf-bases.

*Aspect/angle from vertical*.—Average 17.5 degrees.

*Main stem length*.—Average 6.5 cm.

*Main stem diameter*.—Average 0.8 cm.

*Main stem internode length*.—Average 1.7 cm.

*Pubescence*.—None.

*Luster*.—Glossy.

*Strength*.—Strong.

*Color, juvenile*.—146D (yellow-green).

*Color, mature*.—146C (yellow-green) and tinged 177C (greyed-orange).

*Color at internodes*.—146C (yellow-green) and tinged 177C (greyed-orange).

Foliage:

*General description*.—Epiascidiate; a modified leaf that is comprised of a lower leaf zone, or lamina, and an upper leaf zone, or pitcher, connected between by a pedicel structure.

*Compound or single*.—Single.

*Attachment*.—Petiolate.

*Arrangement*.—Alternate.

*Number of leaves per stem*.—7.

*Whole leaf length*.—Average 24.4 cm.

*Lamina*.—Shape: Oblong to broad oblong. Length: Average 20.2 cm. Width: Average 10.2 cm. Aspect/angle to stem: 70 degrees. Aspect: Slightly carinate. Apex: Broad, abruptly acute and ending in a short pedicel attached to the pitcher. Base: Attenuate. Margin: Entire and coarsely undulate. Texture, adaxial surface: Smooth and glabrous. Texture, abaxial surface: Smooth and glabrous with the exception of the midrib which is moderately pubescent with very short soft hairs; hairs average 0.5 mm in length and are colored green-white and greyed-red, but too minute to accurately discern RHS designation. Luster, adaxial surface: Glossy. Luster, abaxial surface: Moderately glossy. Color: Juvenile lamina, adaxial surface: 144A (yellow-green), however slightly darker and more intense. Juvenile lamina, abaxial surface: A blend of near 144A and 144B (yellow-green). Mature lamina, adaxial surface: A blend of 143A and 146A (green to yellow-green), however slightly darker and more intense. Mature lamina, abaxial surface: Between 146B and 146C (yellow-green). Venation: Pattern: Camptodrome. Color, adaxial surface: 146D (yellow-green). Color, abaxial surface: 144B and 144C (yellow-green).

*Pedicel*.—Length: Average 11.1 cm. Diameter: 0.3 cm. Pubescence: Dense and soft pubescence with hairs having an average length of 0.75 mm and colored 156A and 156B (greyed-white). Luster, upper surface and lower surface: Matte. Color: Juvenile pedicel, upper surface: 165B (greyed-orange). Juvenile pedicel, lower surface: 165B (greyed-orange). Mature pedicel, upper surface: 146D (yellow-green) and tinged 153A, pedicel fading to 177B (greyed-orange) towards the distal end adjacent to the pitcher. Mature pedicel, lower surface: 146D (yellow-green) and tinged 153A, pedicel fading to 177B (greyed-orange) towards the distal end adjacent to the pitcher.

*Pitcher*.—Shape: Cylindrical body and an open pitcher lid at the top. Length or height: Average 19.4 cm. Diameter: Average 3.0 cm. Aspect: Hanging near vertical. Pitcher body: Shape: Cylindrical. Texture, upper surface: Smooth with moderately soft pubescence with very short adpressed hairs having an average length of 0.2 mm (and shorter), and sparsely pubescent with longer hairs having an average length of 1.0 mm; all hairs are colored 199D (greyed-brown). Texture, lower surface: Smooth and glabrous. Luster, upper surface: Matte. Luster, lower surface: Moderately glossy. Pitcher body wings: Two axial ridges (i.e. wings) are present along the back side of the pitcher body, colored 166A (greyed-orange) and fading 146C (yellow-green) towards the top; wings are raised approximately 0.3 cm in height and covered with a fringe of hairs approximately 0.5 cm in length. Color: Upper surface: 194B (greyed-green) and slightly dotted N186A (greyed-purple) near the top; top margin or edge around opening 187A (greyed purple). Lower surface: 200B and 200C (brown), and tinged 146C (yellow-green) towards the base of the pitcher; top margin or edge around opening 187A (greyed purple). Venation: Pattern: Camptodrome. Color, upper surface: 191A and 191B (greyed-green). Color, lower surface: 200A (brown). Pitcher lid: General description: Broad ovate in shape with an average of two strigose hairs having an average length of 0.9 cm; at the base of the lid on the underside, a single hooked soft thorn is present having an average length of 0.7 cm and an average width of 0.3 cm. Length: Average 4.3 cm. Width: Average 3.9 cm. Color: Upper surface: 177A and 177B (greyed-orange), center of the lid tinged 146D (yellow-green) and finely dotted 200B (brown); hooked soft thorn colored 200A (brown) and margined 183A (greyed-purple). Lower surface: Slightly darker than 166A (greyed-orange); strigose hairs at the base of the lid colored 199C (grey-brown).

*Petioles*.—Base: Decurrent. Shape: V-shaped. Length: Average 7.6 cm. Diameter: Average of 1.3 cm horizontally and 0.9 cm vertically. Texture, upper surface: Smooth and glabrous. Texture, lower surface: Moderately pubescent with very short soft hairs; hairs are 0.5 mm in length and colored close to 161A to 161C, but too minute to accurately discern RHS designation. Luster, upper surface: Slightly glossy. Luster, lower surface: Matte. Strength: Strong. Color, upper surface: 143A (green) and slightly darker. Color, lower surface: 146C (yellow-green) and edged 176A and 176B (greyed-orange).

Inflorescence: Inflorescence has not been observed.

Temperature tolerances: USDA Zones 11 to 13; at least tolerant of temperatures to 40 degrees Celsius.

Rain tolerance: Moderate to high.

Wind tolerance: Low.

Disease and pest tolerance: No claims are made to any superior disease or insect resistance or tolerance.

COMPARISON WITH THE PARENT PLANTS

The new *Nepenthes* cultivar 'NP8016' can be distinguished from its female or seed parent *Nepenthes truncata* in the following characteristics described in Table 1 below.

TABLE 1

| Characteristic | 'NP8016' | Seed Parent |
|---|---|---|
| Plant habit | Compact, broad spreading-upright; basal branching only, no lateral branching | Large rosette, becoming a massive climbing plant |
| Plant size (18-month-old plant) | Average 26.8 cm in height and 53.3 cm in spread | Much larger; rosettes and pitchers significantly bigger (pitchers up to approximately 40 cm) |
| Vigor | Moderate vigor | High vigor, strong growth |
| Leaf type | Epiascidiate with a distinct lower lamina leaf zone and cylindrical upper pitcher zone | Broad, truncate (heart-shaped) leaves; non-epiascidiate |
| Leaf size (lamina) | Approx. 20.2 cm in length and 10.2 cm in diameter | Large, thick and broad; not divided into zones |
| Pitcher dimensions | 19.4 cm in length and 3.0 cm in diameter | Up to approximately 40 cm tall, broader and more robust |
| Picher shape | Cylindrical, two fringed rear axial ridges | More bulbous, wings on the front with no rear fringed ridges |
| Pitcher color | Grey-green with grey-purple spotting and a grey-orange lid | Green with red-brown peristome and a spotted interior |
| Pitcher lid | Broad-ovate with small strigose hairs and a single hooked thorn on the underside | Ovate with a basal crest and lacking a short, hooked thorn |
| Pubescence | Moderate, short grey-brown hairs on the pitchers and dense hairs on the pedicel | Less dense indumentum; not strongly pubescent |
| Leaf color (lamina) | Green to yellow-green | Medium to bright green |

The new *Nepenthes* cultivar 'NP8016' can be distinguished from its male or pollen parent *Nepenthes lingulata* in the following characteristics described in Table 2 below.

TABLE 2

| Characteristic | 'NP8016' | Pollen Parent |
|---|---|---|
| Plant habit | Compact, broad spreading-upright; basal branching only, no lateral branching | Slender climber, up to approximately 8 meters |
| Leaf size and shape | Oblong to broad; approx. 20.2 cm in length and 10.2 cm in diameter | Rosette leaves, lanceolate, up to approx. 9.6 cm in length and 3.0 cm in diameter |
| Pitcher dimensions | Approx. 19.4 cm in length and 3.0 cm in diameter | Lower pitchers up to approx. 28.0 cm in length and 4.5 cm in diameter; upper pitchers smaller |
| Pitcher shape | Cylindrical, two fringed rear axial ridges | Infundibular/cylindrical; no paired rear fringed ridges |
| Pitcher color | Grey-green with grey-purple spotting and a grey-orange lid | Usually dark purple to nearly black |
| Pitcher lid | Broad-ovate with small strigose hairs and a single hooked thorn on the underside | Long filiform "tongue" appendage to approx. 4.0 cm |
| Pubescence | Moderate, short grey-brown hairs on the pitchers and dense hairs on the pedicel | Very dense woolly hairs with stellate hairs present |
| Leaf color (lamina) | Green to yellow-green | Dark green upper surface and pale green lower surface |

COMPARISON WITH RELATED KNOWN VARIETY

The new *Nepenthes* cultivar 'NP8016' can be distinguished from the related known variety of *Nepenthes* 'Rebecca Soper' (unpatented) in the following characteristics described in Table 3 below.

TABLE 3

| Characteristic | 'NP8016' | 'Rebecca Soper' |
|---|---|---|
| Vigor | Moderate vigor | Very vigorous and robust |
| Plant habit | Compact, broad spreading-upright; basal branching only, no lateral branching | Vining habit up to 3.0 meters in length, usually hanging or climbing |
| Plant size (18-month-old plant) | Average 26.8 cm in height and 53.3 cm in spread | Larger, medium to large size |
| Leaf type | Epiascidiate with a distinct lower lamina leaf zone and cylindrical upper pitcher zone | Simple green leaves; non-epiascidiate |
| Leaf size (lamina) | Approx. 20.2 cm in length and 10.2 cm in diameter | Narrower and smaller |
| Pitcher dimensions | Approx. 19.4 cm in length and 3.0 cm in diameter | Medium-sized pitchers; approx. 10.0 cm in length and 15.0 cm in diameter |
| Pitcher shape | Cylindrical, two fringed rear axial ridges | Tubular and curved with no rear fringed ridges |
| Pitcher color | Grey-green with grey-purple spotting and a grey-orange lid | Deep red to burgundy and sometimes red-green gradient |
| Pitcher lid | Broad-ovate with small strigose hairs and a single hooked thorn on the underside | Simple lid with no distinctive hooked thorn on the underside |
| Pubescence | Moderate, short grey-brown hair on the pitchers and dense hairs on the pedicel | Generally smooth pitchers |

What is claimed is:

1. A new and distinct cultivar of *Nepenthes* plant named 'NP8016', substantially as illustrated and described herein.

* * * * *